US00PP32526P2

(12) United States Plant Patent
Cherry

(10) Patent No.: US PP32,526 P2
(45) Date of Patent: Nov. 24, 2020

(54) ***CUPHEA* PLANT NAMED 'CUPP1752'**

(50) Latin Name: *Cuphea ignea*
Varietal Denomination: CUPP1752

(71) Applicant: Robert Cherry, Gawler (AU)

(72) Inventor: Robert Cherry, Gawler (AU)

( * ) Notice: Subject to any disclaimer, the term of this patent is extended or adjusted under 35 U.S.C. 154(b) by 0 days.

(21) Appl. No.: 16/887,104

(22) Filed: May 29, 2020

(51) Int. Cl.
*A01H 5/02* (2018.01)
*A01H 6/00* (2018.01)

(52) U.S. Cl.
USPC ..... Plt./420

(58) Field of Classification Search
USPC ..... Plt./420
See application file for complete search history.

*Primary Examiner* — Susan McCormick Ewoldt
(74) *Attorney, Agent, or Firm* — Barbara Campbell; Weatherly IP Solutions, LLC

(57) ABSTRACT

A new and distinct variety of *Cuphea* named 'CUPP1752' that is characterized by prolifically self-branching dense and compact plant habit, dark green leaves with contrasting pale grey-green venation, and multicolored white, blushed-orange, scarlet and violet tubular flowers which are borne in profusion, is disclosed.

2 Drawing Sheets

Genus and species: *Cuphea ignea.*
Variety denomination: 'CUPP1752'.

BACKGROUND

The present invention relates to a new and distinct cultivar of *Cuphea* grown as an ornamental plant for use in the garden, in planted containers and in the landscape. The new variety from the family Lythraceae is known botanically as *Cuphea ignea* and is commonly termed the cigar plant. The new invention will be referred to hereinafter by the cultivar name 'CUPP1752'.

In 2007, the inventor began to assemble at his nursery in Kulnura, New South Wales, Australia a collection of species and seedlings of various *Cuphea* plants including unnamed plants of *Cuphea ignea*. The plants in the collection were exposed to open-pollination and further plants were raised from collected seed. In 2013, the inventor observed that one such seedling, now identified as 'CUPP1752', bore flowers whose flower tube is white at the base whereas the flower tubes of any of the possible parent seedlings were orange-red in color as is typical of the species *Cuphea ignea*. The parents of 'CUPP1752' were unnamed seedlings previously raised by the inventor.

The inventor carried out the first asexual propagation of 'CUPP1752' in 2013, using vegetative tip cuttings in Kulnura, New South Wales, Australia. The inventor has since determined that 'CUPP1752' is stable and reproduces true-to-type in successive generations of asexual propagation via vegetative tip cuttings.

SUMMARY

The following traits have been repeatedly observed and represent the distinguishing characteristics of the new *Cuphea* variety named 'CUPP1752'. These traits in combination set 'CUPP1752' apart from all other existing varieties of *Cuphea* known to the inventor. 'CUPP1752' has not been tested under all possible conditions and phenotypic differences may be observed with variations in environmental, climatic, and cultural conditions without however any variance in genotype.

1. 'CUPP1752' is prolifically self-branching and forms a dense and compact mounding plant habit.
2. 'CUPP1752' is exceptionally compact in terms of its width or spread. After one year's growth, 'CUPP1752' is 30 cm in diameter and when mature in the landscape, is 50 cm to 60 cm in diameter.
3. 'CUPP1752' bears tubular flowers at each node in profusion year-round.
4. The flower tubes of 'CUPP1752' are bi-colored, being white towards the base, blushed orange towards the apex.
5. The apex or mouth of the floral tube of 'CUPP1752' is flared and multicolored scarlet, violet and cream-yellow.
6. Up to six light green tiny petal (or petal-like) appendages are affixed and outward-facing to the apex or mouth of the floral tube.
7. The flowers of 'CUPP1752' are self-cleaning, falling off the plant while still colorful. In consequence, plants of 'CUPP1752' bear only fresh and brightly colored flowers.
8. The leaves of 'CUPP1752' are dark green in color with contrasting pale grey-green veins on the upper surface.
9. 'CUPP1752' is hardy to USDA Zone 10.

DESCRIPTION OF THE DRAWINGS

The accompanying color photographs illustrate the overall appearance of the new *Cuphea* variety named 'CUPP1752' showing the color as true as is reasonably possible to obtain in color reproductions of this type. Colors in the photographs may differ from color values cited in the detailed botanical description, which accurately describe the actual color of the new variety 'CUPP1752'.

FIG. 1 shows a plant of 'CUPP1752' growing in a 1-gallon container.

FIG. 2 shows a close-up view of a flowering stem of 'CUPP1752'.

DESCRIPTION OF THE NEW VARIETY

Figure 1:
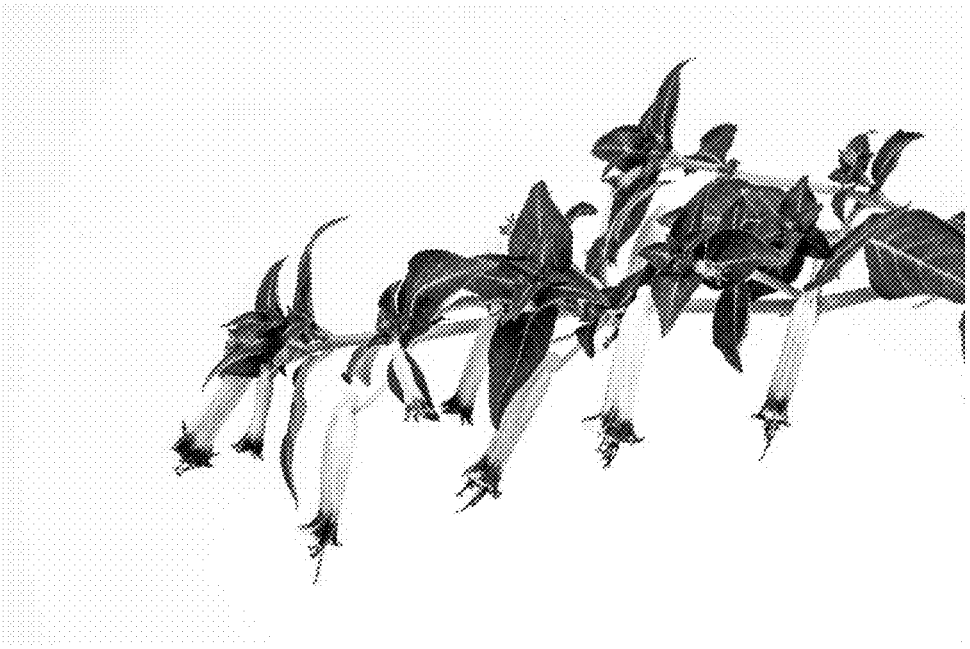
FIG. 1 and FIG. 2 have been made by clear-cutting of a photograph taken in October 2019 of a plant growing in an unheated greenhouse in Oxnard Calif.
Figure 2:
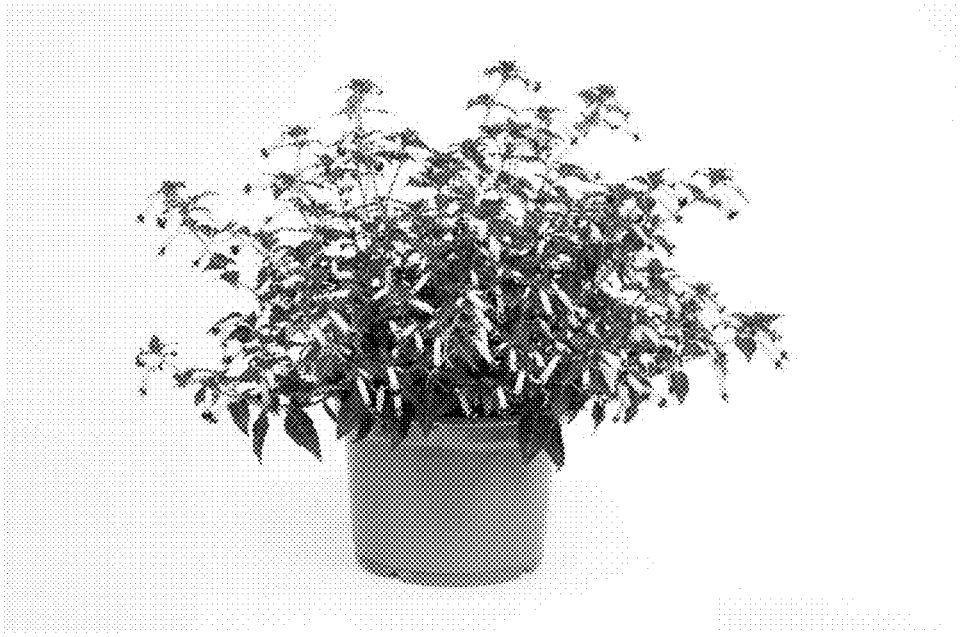
Figure 3:
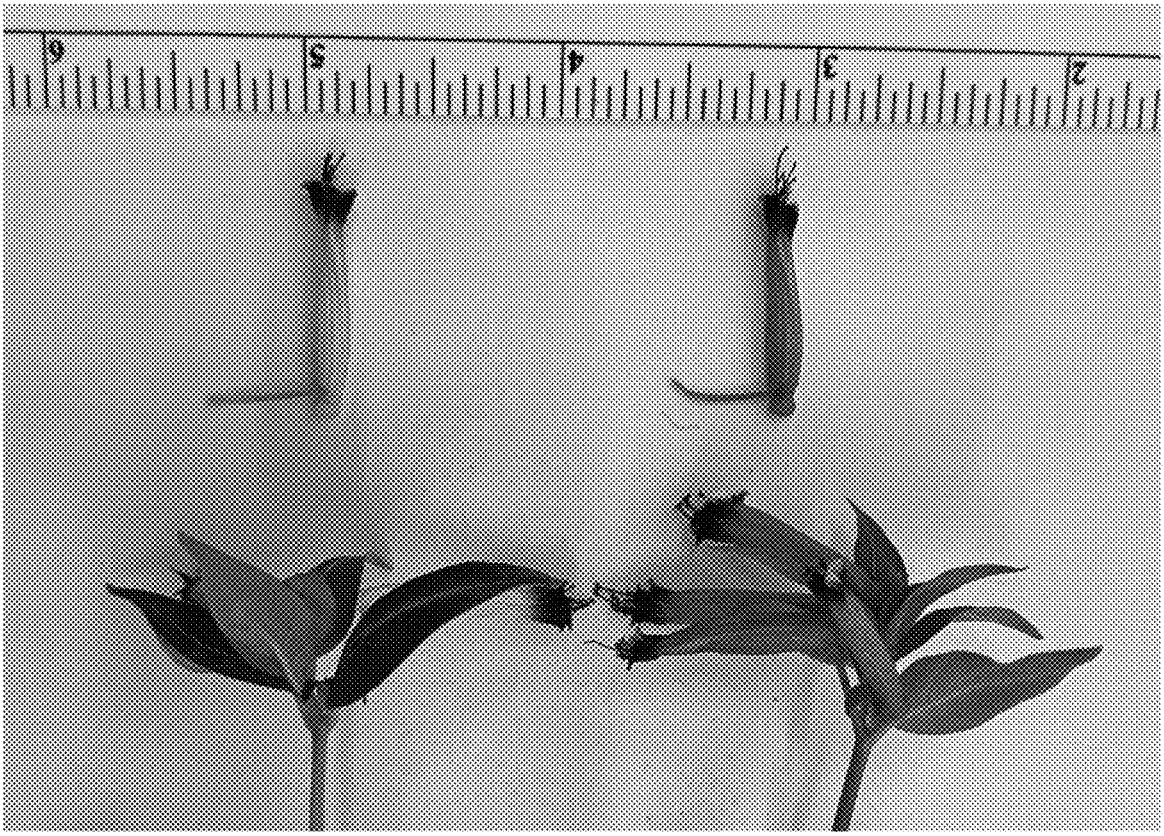
FIG. 3 shows 'CUPP1752' on the left alongside the comparison variety *Cuphea* 'Firecracker' (unpatented) on the right. The scale in the drawing is a scale in inches. The drawing was made from plants growing at the inventor's nursery in Kulnura, New South Wales, Australia.

The following is a detailed botanical description of the new *Cuphea* cultivar named 'CUPP1752'. Observations and measurements were collected in Santa Barbara, Calif., from 9-month-old plants grown out of doors. Color determinations are made in accordance with the Fifth Edition (2007) of The Royal Horticultural Society Colour Chart from London, England, except where general color terms of ordinary dictionary significance are used.

Botanical classification:

*Family*.—Lythraceae.

*Genus*.—*Cuphea*.

*Species*.—*Hybrida*.

*Denomination*.—'CUPP1752'.

*Common name*.—Cigar plant.

Parentage: *Cuphea hybrida* 'CUPP1752' is a hybrid resulting from the open-pollination of seedlings of the species *Cuphea ignea*.

Plant:

*Habit*.—Dense, compact, mounding.

*Commercial category*.—Ornamental.

*Use*.—For garden and landscape.

*Suggested commercial container size*.—1-gallon container.

*Propagation method*.—Vegetative cuttings.

*Rooting system*.—Fine.

*Vigor*.—Highly vigorous and naturally self-branching.

*Crop time*.—4 months to produce a 1-gallon container from taking an initial cutting.

*Plant dimensions*.—After 15 weeks from planting a rooted cutting into a 1 gallon container, 'CUPP1752' achieves a height of 20 cm and a spread of 30 cm. When fully established in the landscape, 'CUPP1752' achieves a height of 50 cm and a spread of 50 cm to 60 cm in width.

*Cultural requirements*.—Grow in full sun to part shade.

*Pest or disease resistance*.—None known to the inventor.

*Pest or disease susceptibility*.—None known to the inventor.

*Hardiness*.—USDA Zone 10.

*Special considerations*.—Blooms continually throughout the year in USDA Zone 10.

Stem (main stem, primary branches, secondary branches):

*Main stem* (*below first pinch at* 5 *cm*).—Shape: Cylindrical. Dimensions: 5 cm in length, 0.5 cm in diameter at soil level. Surface: Rough. Color between N199B and N200A.

*Primary branches*.—Shape: Cylindrical. Dimensions: 15 cm to 20 cm in length, 2 mm to 3 mm in diameter. Internode distance: 2.0 cm to 2.5 cm. Surface: Lightly pubescent becoming smooth, glabrous with age. Color: Ranges between 144C and N144D.

*Secondary branches*.—Shape: Cylindrical. Dimensions: 3 cm in length, 1.5 mm in diameter. Internode distance: 1.0 cm to 1.5 cm. Surface: Lightly pubescent becoming smooth, glabrous with age. Color: Ranges between 144C and N144D. Branch quantity: Very numerous, approximately 50 primary and secondary branches.

Foliage:

*Type*.—Evergreen.

*Leaf arrangement*.—Opposite.

*Leaf division*.—Simple.

*Leaf margin*.—Entire, ciliate. Very fine silver-grey hairs, less than 0.5 mm in length.

*Leaf surface* (*abaxial and adaxial*).—Glabrous.

*Leaf shape*.—Lanceolate.

*Leaf length*.—2.5 cm.

*Leaf width*.—1.5 cm.

*Leaf color* (*adaxial surface*).—139A.

*Leaf color* (*abaxial surface*).—138B.

*Leaf apex*.—Acute.

*Leaf base*.—Attenuate.

*Venation*.—Pinnate.

*Vein color* (*adaxial surface*).—194D, midrib prominent and contrasting.

*Vein color* (*abaxial surface*).—139A, slightly raised.

*Attachment*.—Petiolate.

*Petiole shape*.—Cylindrical.

*Petiole surface*.—Puberulent.

*Petiole color*.—Ranges between 144C and N144D.

*Petiole dimensions*.—1.0 mm to 1.5 mm length, 1 mm. in width.

*Leaf fragrance*.—None observed.

Inflorescence:

*Inflorescence* (*axillary and terminal*).—Solitary flower.

*Inflorescence structure*.—Modified calyx whose six sepals are completely fused into a floral tube. Petals absent or present as tiny ear-like appendages attached at apex of floral tube.

*Inflorescence shape*.—Narrow tubular, widening towards apex. Tube terminates at base with globular nectar sac.

*Inflorescence aspect*.—Downward, approximately 45 degrees below the horizontal.

*Inflorescence quantity*.—Very numerous, typically 10 to 15 flowers per stem, approximately 300 flowers per plant at any one time.

*Blooming season*.—Year round if frost-free and unshaded.

*Inflorescence dimensions*.—2.5 cm in length, 3 mm in diameter at base, 5 mm in diameter at apex.

*Inflorescence color* (*mature flowers, adaxial surface*).—Nectar sac and approximately one-third of entire tube length from base: NN155D to NN155B. Midpoint of the tube, extending to just below and at the flared apex: 35B to 50B. Flared apex: 42A, 59A, 11A and 11D are all individually present.

*Inflorescence color* (*mature flowers, abaxial surface*).—11D.

*Inflorescence surface*.—Glabrous.

*Inflorescence apex*.—Flared, with up to six outward-facing tiny petal appendages.

*Peduncle color*.—178D, except 144C towards stem.

*Peduncle dimensions*.—8 m to 11 mm in length, 1 mm. in diameter.

*Peduncle shape*.—Cylindrical.

*Peduncle surface*.—Pubescent.

*Petals*.—Typically six in number, occasionally for or five.

*Petal attachment*.—At rim of apex, located at each fused sepal junction, outward-facing.

*Petal dimensions*.—2 mm in length, 1.5 mm in width, apex rounded, margins entire, surface glabrous.

*Petal color* (*both surfaces*).—140A.

*Inflorescence persistence*.—Self-cleaning.

*Inflorescence fragrance*.—None observed.

*Lastingness of inflorescence* (*range*).—3 to 5 days.

Reproductive organs:

*Stamens*.—Quantity: 10 adnate to floral tube. Length: Ranges between 3 mm (stamens entirely inside floral tube) and 11 mm (stamens strongly exerted above floral tube apex). Diameter: 1 mm. Color: N92A or darker towards 203C. Anthers: Ovoid, dorsifixed, 2 mm in length, 1 mm in width, color as stamens, N92A to 203C. Pollen: None observed.

*Pistil quantity*.—1.

*Pistil dimensions*.—2.5 cm in length, 1 mm in diameter.

*Pistil color*.—54A becoming 203C towards and immediately beneath stigma.

*Stigma*.—Miniscule, hemispherical, diameter very slightly greater than diameter of pistil at attachment.

*Stigma color*.—54A. Ovary position: Superior. Ovary shape: Ovoid. Ovary dimensions: 1.5 mm in height, 2 mm in diameter. Ovary color (observed immature): 145B.

COMPARISON WITH PARENTAL LINES AND KNOWN VARIETY

'CUPP1752' is distinguishable from its parents and in general from the species *Cuphea ignea*, by flower color, by the color of the young stems and by the color of the leaves. Whereas 'CUPP1752' bears flowers whose flower tube is white at the base, becoming blushed orange towards the apex, the flower tubes of the parents, the species and other known varieties are predominantly orange-red in color. The young stems of 'CUPP1752' are green in color, whereas the young stems of the parents and the species are grey-red in color. The leaves of 'CUPP1752' are dark green in color, whereas the leaves of the parents and the species are mid-green in color.

The variety of *Cuphea* which the inventor considers most closely to resemble 'CUPP1752' is an old variety of *Cuphea* known in Australia as *Cuphea* 'Firecracker' (unpatented). This variety is not the same variety as a *Cuphea* plant also named 'Firecracker' (U.S. Plant Pat. No. 13,595). The comparison variety 'Firecracker' (unpatented) exhibits a similar very compact habit (30 cm in width after one year) to 'CUPP1752' but differs by flower color and the color of the young stems and the foliage. Whereas 'CUPP1752' bears flowers whose flower tube is white at the base, becoming blushed orange towards the apex, the flower tubes of 'Firecracker' (unpatented) are predominantly orange-red in color. The young stems of 'CUPP1752' are green in color, whereas the young stems of 'Firecracker' (unpatented) are grey- red in color. The leaves of 'CUPP1752' are dark green in color, whereas the leaves of 'Firecracker' (unpatented) are mid-green in color.

I claim:

1. A new and distinct variety of *Cuphea* plant named 'CUPP1752' as described and illustrated herein.

* * * * *